United States Patent
Srivastava et al.

(10) Patent No.: US 10,610,312 B2
(45) Date of Patent: Apr. 7, 2020

(54) MODULAR INTERFACE FOR A ROBOTIC SYSTEM

(71) Applicant: Sudhir Prem Srivastava, Midland Texas, TX (US)

(72) Inventors: Sudhir Prem Srivastava, Midland Texas, TX (US); Sugumar Perumalsamy, Madurai (IN); Hardik Sharma, Bikaner (IN)

(73) Assignee: SS Innovations China Co., LTD, Hangzhou, Zhejiang (CN)

( * ) Notice: Subject to any disclaimer, the term of this patent is extended or adjusted under 35 U.S.C. 154(b) by 935 days.

(21) Appl. No.: 15/027,695

(22) PCT Filed: Oct. 6, 2014

(86) PCT No.: PCT/IB2014/065083
§ 371 (c)(1),
(2) Date: Apr. 7, 2016

(87) PCT Pub. No.: WO2015/052629
PCT Pub. Date: Apr. 16, 2015

(65) Prior Publication Data
US 2016/0235490 A1  Aug. 18, 2016

(30) Foreign Application Priority Data

Oct. 7, 2013 (IN) .......................... 2970/DEL/2013

(51) Int. Cl.
*A61B 34/30* (2016.01)
*A61B 46/10* (2016.01)
*A61B 17/00* (2006.01)

(52) U.S. Cl.
CPC .............. *A61B 34/30* (2016.02); *A61B 46/10* (2016.02); *A61B 2017/00477* (2013.01)

(58) Field of Classification Search
CPC ......... A61B 34/30; A61B 34/32; A61B 34/37; A61B 34/70; A61B 34/71; A61B 34/74; A61B 46/10; A61B 2017/00477; A61B 2034/301–306; A61B 2034/731–733
See application file for complete search history.

(56) References Cited

U.S. PATENT DOCUMENTS

2007/0137371 A1* 6/2007 Devengenzo ............ B25J 15/04
74/490.01

\* cited by examiner

*Primary Examiner* — Erich G Herbermann

(57) ABSTRACT

The disclosure is directed to a medical robotic system and method for releasably securing a medical instrument over a modular support assembly that is further removably coupled to the manipulating arm via an intermediate fastening component. The medical instrument is configured for delivery through a small percutaneous penetration in a patient as it slides over the modular support assembly, independent of the manipulating arm. The robotic system further includes a simplified draping mechanism including covering the manipulating arm up to the fastening component thereby obviating the need for extensive sterile drape that extends all over the arm up to the support interface and the cannula holding assembly in existing art. Advantageously, the present invention allows for a quick and simple installation while allowing for free rotary motion of the support assembly.

16 Claims, 5 Drawing Sheets

MODULAR INTERFACE FOR A ROBOTIC SYSTEM

FIELD OF THE INVENTION

The present disclosure generally relates to robotic system and method enabling minimally invasive surgery (MIS), and more particularly, to techniques of enhancing robotic surgical procedures with improved interfacing arrangement for maneuvering surgical instrument over the operative area of the patient with enhanced dexterity.

BACKGROUND OF THE INVENTION

Minimally invasive surgical techniques have been adopted worldwide to replace conventional surgical procedures that reduce the amount of extraneous tissue that may be damaged during surgical or diagnostic procedures, thereby reducing the patient recovery time, discomfort, prolonged hospital stays and particularly deleterious side effects. Typically, medical robotic systems require a close coupling between the robotic manipulators and the surgical instrument defining the end effectors configured to be delivered through a small percutaneous penetration in a body cavity.

Heretofore, the coupling mechanism in surgical robotic systems comprises a driving unit to transfer the controlling motions from the functional end of the robotic arm to the detachably attached surgical instrument and to make the instrument separately sterilizable for use during the course of performing the surgery. Furthermore, the coupling enhances significantly the safety, accuracy, dexterity and speed of minimally invasive and other robotically enhanced procedures. However, in the most commonly employed configurations, the coupling mechanism has a finite range of motion owing to the arrangement of components on its either side that are configured for transferring electro mechanical signals from the robotic arm to the surgical instrument. The limitation in motion adversely hampers the free movement of the coupling arrangement, so necessitated during the surgery. Now, in order to compensate for the undue loss in free motion of the coupling arrangement, the robotic arm may have to traverse an undesirable broader course that may enhance probability of potential conflict between said arms.

Furthermore, necessitating the presence of driving unit to actualize the motion of the surgical instrument is ostensibly cumbersome, as it creates an additional dependency of the surgical instrument upon the driving unit to be operable, which is uncalled-for, especially in a scenario where the attempt is to make the system flexible and modular to minimize the floor occupancy area, or alternatively enhance the robotic arm mobility area with minimum risk of collision or conflict with other robotic arms.

The robotically assisted medical systems utilize a sterile barrier to separate the non sterile robotic arm from the mandatorily sterile surgical instrument operating environment. This sterile barrier often includes a sterile plastic drape that envelops the robotic arm and a sterile adaptor that operably engages with a sterile surgical instrument in a sterile field and non sterile manipulator arm, and includes a flexing drape interface to retain a drape section therebetween such that while the torque and other force feedbacks is received as an input from both the surgical instrument as well as the robotic arm, the sterile barrier is maintained between the sterile surgical instrument and the non-sterile robotic system. Also, the portion of same sterile drape shields the cannula adaptor effectively such that the non exposed portion of adaptor remains sterile.

However, many new challenges are posed with the present aforesaid technique. For example, the drape interface if not properly aligned or dressed over the instrument supporting assembly, instrument or cannula adaptors, may get entangled, and interfere with the motion of the surgical instrument. There always remains a concern of unfolding drape over the cannula adaptor and forming a sag in drape at the cannula mount area, still folding the excess drape back enough to closely fit the shape of the cannula holding assembly and preserve sterility. Additionally, the sterile adaptors disadvantageously involve complex assembly of various intricate components for coupling with corresponding complementary arrangements on the manipulator arm on one side and the surgical instruments on the other, thereby making the whole process costly and cumbersome.

In the light of aforementioned challenges, what is needed, therefore, is a robotically assisted or tele-robotic assembly that allows easy detachability of surgical instruments or diagnostic devices during performance of surgery without breaking the sterile barrier while reducing the complexity of any sterile adaptor. Moreover, from a cost perspective, it would be preferable to have sterilizable modular interface, thus requiring the system to be simpler so as to allow unobstructed movement of the surgical instrument for enhanced precision and control.

SUMMARY OF THE INVENTION

According to the present disclosure there is provided a medical robotic system comprising: at least one manipulating arm having a manipulating end; at least one medical instrument; a modular support assembly removably coupled to the manipulating end of the manipulating arm via an intermediate sterilizable fastening component, and adapted to releasably secure thereupon the medical instrument to cause slidable displacement of said instrument independent of the manipulating arm.

In one aspect, the modular support assembly is sterilizable and configured to rotate a full 360 degree with respect to the manipulating end. In another aspect of the invention, a simplified draping mechanism for maintaining a sterile barrier between the sterile and non-sterile environment, is proposed. The mechanism facilitates free unobstructed motion of the manipulating arm, eliminating any over constraint on drape or any twisting thereof with rotary movement of the manipulating end.

DETAILED DESCRIPTION OF THE INVENTION

Figure 1:
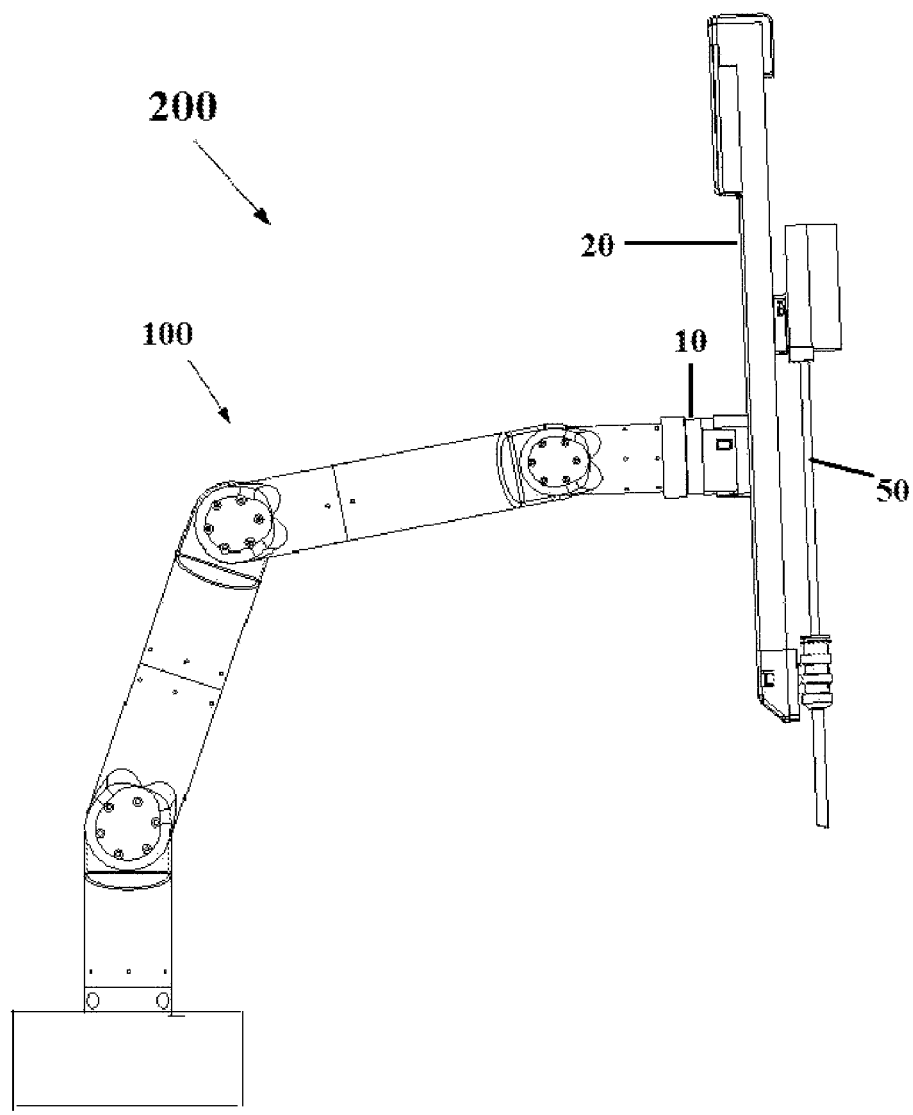
FIG. 1 illustrates a simplified view of medical robotic system with mounted modular support assembly in accordance with an embodiment of the present invention.

Some embodiments of this invention referring to the drawings in details wherein like numerals indicate like elements, and illustrating all its features, as will be described in more detail hereinbelow.

In one general aspect, embodiments of the present disclosure are directed to a modular, light weight and sterlizable medical robotic system for performing a tele-robotic minimally invasive surgery (MIS). As shown schematically in FIG. 1, the medical robotic system generally includes one or more articulated arms, exact number dependent on the type of medical or surgical procedure to be performed among many other factors. In a preferred embodiment, the articulated arm is supported onto the operating table that allows the arm to slidably move along the rails for reaching the remote internal surgical site, or is positioned adjacent to the patient body while performing procedures on the patient.

Now that a preferred embodiment of the medical robotic system will be described in detail, numerous variations and modifications will suggest themselves to a person skilled in the relevant arts, that the here-below discussed medical robotic system, though can be extended for its usage across all medical procedures involving articulated robotic system, here, for the purposes of establishing exemplary embodiments, is interchangeably used with term surgical robotic system. Likewise, the medical instruments used for performing medical procedure and surgical instruments are interchangeably used further herein.

The surgical system 200 includes a non-sterile articulated arm 100 with a sterlizable surgical instrument support member 20 in connection therewith, a sterlizable medical/surgical instrument 50 and an intermediate fastening component 10, as illustrated in FIG. 1. The articulated arm 100 generally includes a surgical instrument support member 20 (will be referred as support member 20, hereon) removably mounted thereto and adapted to releasably secure thereupon the surgical instrument 50. The articulated arm 100 in conjugation with the support member 20 is capable of supporting wide range of surgical instruments to conduct useful medical interventions. These tools are removable and replaced repeatedly during surgery which may expose the sterile environment to possible cross contamination. To avoid such contamination, the present disclosure provides an intermediate fastening component 10 for coupling the support member 20 to the manipulating end 100(a) of the robotic arm 100.

Unlike, in standard robotically-assisted surgery wherein the operational position of surgical instrument is controlled by a drive assembly enclosed within the housing of robotic arm and requires proportional coordinated movements between the surgical instrument and the articulated arm; the present disclosure is particularly useful for controlling the surgical instruments at the surgical site independent of the relative proportional movements of the entire robotic arm. This is achieved by involving an instrument support member 20 of modular construction and an intermediate fastening component 10, as will be explained later.

A suitable intermediate fastening component 10, generally including, a mechanical arrangement of components that mechanically and electrically couples the support member 20 to the manipulating end 100(a) of the articulated arm 100, is discussed in detail later. Stated simply, this configuration, not only provides modularity to the surgical system 200 as the rotary motion of the manipulating end 100(a) of the articulated manipulating arm is transferred thereto, but also provides ease in maintaining sterility of the system with simple draping mechanism, as will be discussed in detail below.

As shown in FIG. 1, the manipulating end 100(a) or the end effector of articulated arm 100 couples with an intermediate fastening component 10 that separates non sterile articulated arm field from the sterile surgical instrument support member 20 and the surgical instrument 50 field. In one exemplary embodiment, a sterlizable, light weight intermediate fastening component 10 may be used to provide a sterile surgical environment. The sterile drape extends substantially over the entire articulated arm 100 and at least a portion of the intermediate fastening component 10 such that the non exposed portion of the intermediate fastening component remains sterile when extended into the sterile field of the surgical site. The intermediate fastening component 10 is sterilizable, ETO and autoclavable. The mechanical and electrical components assembled therein enables transmission of motion feed-through and electrical signals from the articulated arm 100 to the support member 20.

The intermediate fastening component 10 in conjugation with the articulated arm 100 provides full and continuous motion to the support assembly 20 in counterclockwise and clockwise directions to provide 360-degree full rotation.

Figure 2A:
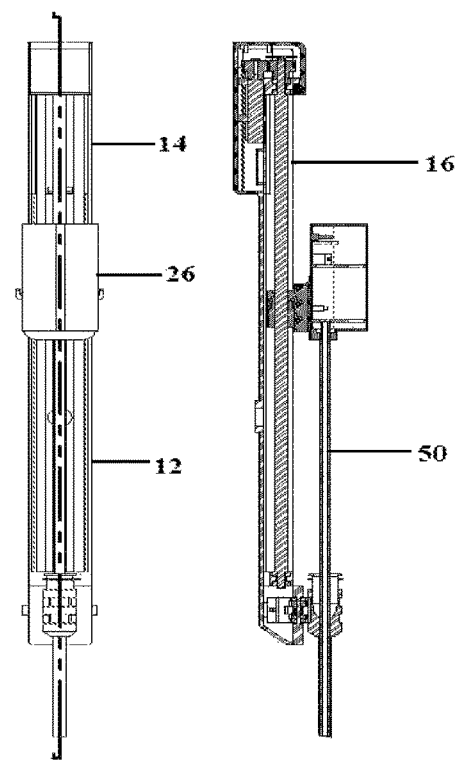
FIG. 2(a) illustrates a cross sectional view of the modular support assembly in accordance with an embodiment of the present invention.

Referring now to FIG. 2(a), the support member 20 comprises an external casing 12 having a first surface 14 and a second surface 16, said first surface 14 defining an axially extending central cavity and a second surface 16 housing thereupon an opening for coupling the support member 20 to the articulated arm via an intermediate fastening component 10. In the preferred embodiment, the external casing 12 is a rigid casing having a proximal end 12(a) and a distal end 12(b), and configured to be orthogonally displaced with respect to the manipulating end 100(a) of the articulated arm 100 during the surgical procedure.

Figure 2B:
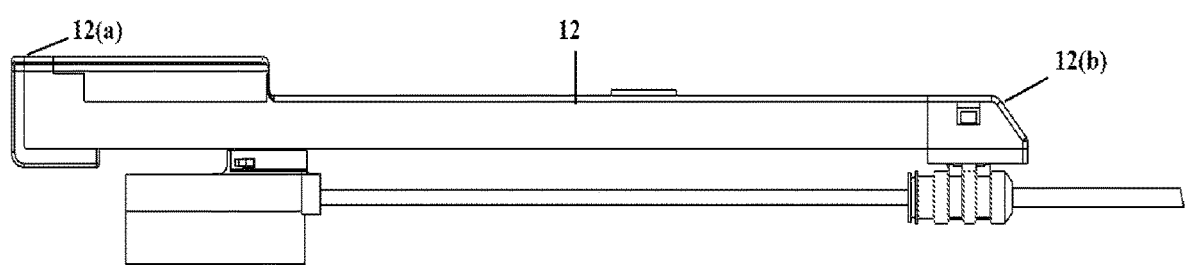
FIG. 2(b) shows a modular support assembly with a tapered trapezoidal bottom for holding the cannula assembly in accordance with one other embodiment of the present invention.

To operate effectively with the system 200, the rigid external casing 12 is provided a curved angular configuration, preferably a trapezoidal configuration, having a flat apex and two opposed downwardly and inwardly sloping legs, towards its distal end 12(b) to avoid the support member 20 to create an impact on the body wall whilst it is displaced with respect to the articulated arm during performance of the surgery, as depicted in FIG. 2(b). However, it will be readily recognized by those skilled in the art that other configurations are also possible.

Figure 3:
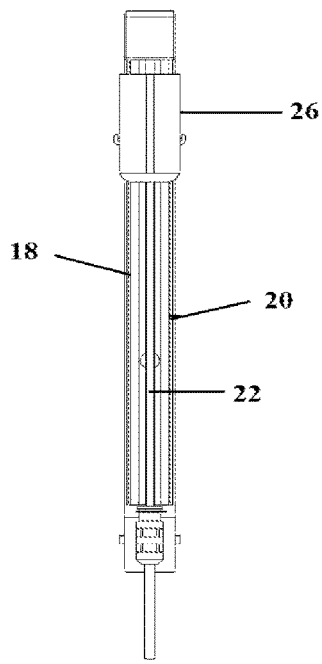
FIG. 3 represents a pair of guide rods and a threaded shaft disposed within the modular support assembly in accordance with an embodiment of the present invention.

As shown in FIG. 3, the central cavity defined in the first surface 14 comprises linear guide rods 18, 19 axially extending between the proximal 12(a) and distal ends 12(b), substantially parallel to each other, within the defined cavity. The threaded shaft 22 positioned relatively in between the guide rods 18, 19 is firmly fixed to the ends of external casing 12(a) and 12(b) via bearings, such as ball bearings, roller bearings, etc. The first surface 14 further includes a movable carriage plate 26 that slides over the guide rods 18, 20 for linear displacement of the surgical instrument 50 with respect to the support member 20.

Figure 4:
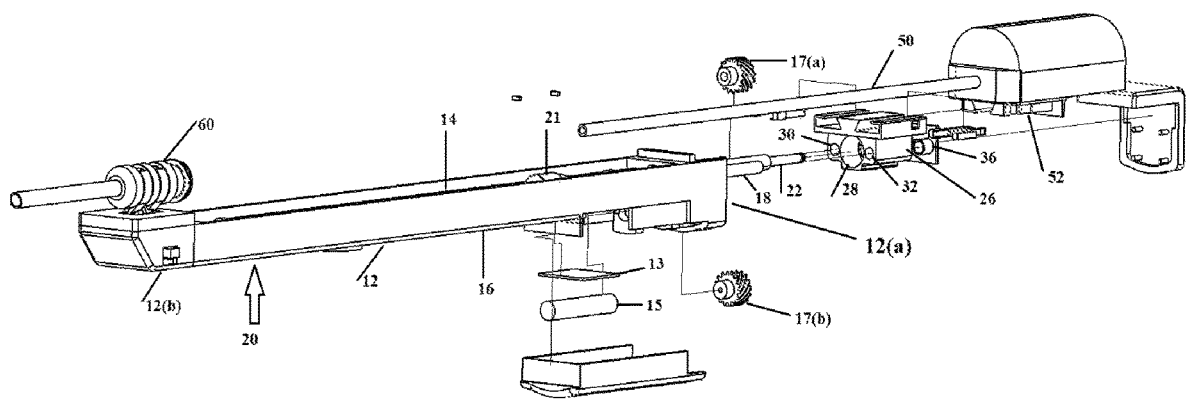
FIG. 4 illustrates an exploded perspective view of the modular support assembly in accordance with an embodiment of the present invention.

In a specific embodiment, so illustrated in FIG. 4, the aforementioned movable carriage plate 26 is provided with a predetermined pattern of generally circular slots on its first surface facing towards the proximal end 12(a) and extending towards the distal end 12(b). The first slot 28 is positioned relatively centrally to allow passage of threaded shaft 22, such as threaded screw or a ball screw, therethrough; and a set of slots 30, 32 for passage of linear guide rods 18 and 19 respectively. A complementing nut, like a ball screw nut 21 embracing the complementarily threaded shaft screw 22 is provided to enable translation of the rotational motion of the threaded shaft 22 into the linear movement of the complementing nut, which further aligns with the carriage plate 26 to carry it along as the nut slides along the threaded shaft.

Each given slot, 30 and 32 of the movable carriage plate 26, on its either end rigidly accommodates linear bearings 36, 38 to facilitate smooth motion of the carriage plate 26 as it slides over the guide rods 18, 19. To this end, this configuration further prevents the carriage plate 26 from moving in the lateral direction with axial and radial loads suitably balanced and to ensure that the carriage plate 26 remains generally centered with respect to the support member 10 during a surgical procedure. The linear guide rods 18, 19 are preferably made of suitably selected sterilizable material, preferably aluminum, plastic or stainless steel. The guide rods, in the most preferred configuration support the carriage plate 26 slidably disposed thereupon rigidly and steadfastly. It should be understood that the disclosure is not limited to the above described means for smooth sliding of the carriage plate 26 over the guide rails 18, 19 and can be suitably modified to achieve the above functionality with the mechanisms known to the person skilled in the art.

The distal end 12(b) of the external casing 12 further supports a cannula holding assembly 27 that allows the surgical instrument 50 to rotate and move axially through its central bore, before entering into the surgical site. The surgical instrument 50 is held with respect to the holding device 20 in a generally longitudinal direction 14, and may be rotatable relative to the proximal housing about its axis, providing the end effector at its distal end with an added degree of freedom within the patient's body. The surgical instrument 50 may include a variety of articulated end effectors, such as jaws, scissors, graspers, needle holders, micro-dissectors, staple appliers, tackers, suction irrigation tools, and clip appliers, or non-articulated instrument, such as cutting blades, probes, irrigators, catheters or suction orifices.

The second holder is positioned at the distal end of the holding device 20 to releasably hold the trocar or the cannula 60 through which the surgical instrument protrudes to reach the body interior, as shown in FIG. 2(a). Whenever the surgical instrument 50 is inserted, it is held in a fixed configuration in a longitudinal direction with respect to the support assembly 20. In particular, the surgical tool 50 slides over the support assembly 20 along the insertion axis relative to the robotic arm, while the remote center of spherical rotation remains fixed at a point along the insertion axis of the surgical instrument, in close proximity to the body wall. The surgical instrument, in accordance with a preferred embodiment, is allowed to rotate along with the associated end effector about its longitudinal axis.

Re-referring to FIG. 4, an embodiment of the support member 20 is illustrated, wherein the second surface 16 of the support member 20, towards its proximal end 12(a), includes an actuating unit-motor housing 15 consisting of at least one motor that remains mounted on the second surface. The output shaft of the motor 15 is attached to a first helical or spur gear 17(a) having teeth that mesh with the teeth of a second helical gear or a spur gear 17(b) that is, in accordance with one embodiment, may be attached or fastened to the threaded shaft 22 such that the rotation of the output shaft of the motor 15 rotates the threaded shaft 22 therewith. The motor housing 15 further houses a printed circuit board 13 wired to the aforementioned motor 15 for controlling and energizing said motor.

The support member 20 is preferably constructed of a light weight, sterilizable material that is capable of withstanding high temperature sterilizable process after each surgical procedure. The modular design of the support member 20 allows its easy disengagement from the non sterile field so that it can be sterilized by conventional methods, such as steam, heat and pressure. It should be noted that although the support member 20 is shown as having a rectangular cross sectional shape in the drawings, the support member 10 could alternatively have a spherical, hemispherical, oval or any other cross sectional shape.

In a specific embodiment, a sensor (magnetic sensor)/limit switch is disposed on the proximal end 12(a) of the external casing 12 facing towards the carriage plate to interact with the sensor disposed within first surface of the carriage plate 26 facing towards the proximal end 12(a). Likewise, the distal end 12(b) of the external casing houses a sensor (magnetic)/limit switch that interact with the sensor disposed within the other end of the carriage plate 26 to define the range of motion of the carriage plate within predefined safety limits. Preferably, the allowable distance that can be travelled by the carriage plate 26 for necessary motion of the surgical instrument 50 is maximum up to 600 mm. An additional sensor may be disposed at the proximal end of the threaded shaft 22 to control the rotation of the threaded shaft 22 within predefined limits.

Now, a mechanism for releasably connecting the surgical instrument 50 to the support member 20 will be illustrated. As is understood from foregoing description, the carriage plate 26 of the support member 20 is configured to releasably mount thereupon the surgical instrument 50 that is required to engage and disengage rapidly during the operation to be replaced with other surgical instrument, as per the need. In one specific configuration, the surgical instrument 50 slides over the carriage plate 26 and engage therewith in a dove tail configuration.

Broadly, the surgical instrument 50 configured to be inserted into a body cavity, comprises a surgical instrument base plate 52 that is slidably disposed over the carriage plate 26, motor housing, printed circuit board, ball bearings, spur or helical gears, encoders, cabling pulleys and idler pulleys which are mentioned herein for the purpose of understanding the full functionality of the support member 20 as it achieves one of its primary objective of releasably securing the surgical instrument 50 thereupon.

Figure 5:
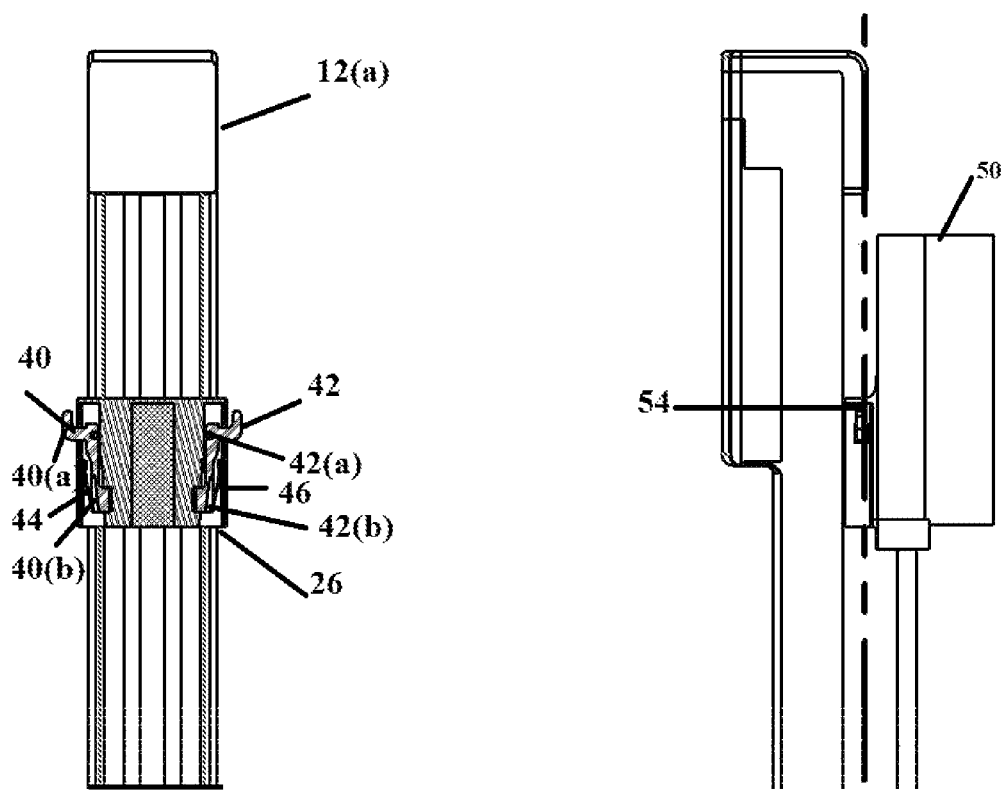
FIG. 5 illustrates mechanism for securing and sliding the medical instrument along the support assembly in accordance with an embodiment of the present invention.

As clearly shown in FIGS. 4 & 5, the carriage plate 26 of the support member 10 that is adapted to receive the base plate 52 of the surgical instrument 50 has a generally ridge and furrow like arrangement, a pair of opposing ears in the form of quick release clip 40, 42 laterally protruding from the carriage plate 26 and pivoted thereto at its first end 40(a), 42(a) so as to prevent its rotation or any free movement, whilst the second end 40(b), 42(b) remains freely movable when not disposed within the locking slots (discussed below), a pair of retractable locking element, like a metal spring 44, 46 positioned along peripheral edges of the carriage plate 26 and bearing a side-to-side abutting relationship with the second end of the quick release clip 40(b), 42(b) to control its movement as required during coupling and de-coupling of surgical instrument 50.

Re-referring to FIGS. 4 & 5, the ridge and furrow like arrangement on the carriage plate 26 engages with a complementary configuration provided on the surgical instrument base plate 52 to allow the surgical instrument slide through the carriage plate and firmly secures thereto as in a dove tail configuration. The base plate 52 is cut into a pair of locking slots at its base, which at least partially accommodates the second end of quick release clip 40(b), 42(b) so as to lock the surgical instrument in place as discussed more in detail below. The retractable locking element is preferably biased towards into the locked position in absence of applied tension. However, whenever the surgical instrument base plate 52 is made to slide over the carriage plate 26, the retractable locking element is displaced from its locked position to an unlock position such that the quick release clips allow the base plate to slide through the carriage plate 26. Once the base plate is accommodated, the retractable locking element resumes its locking position and stabilizes the combination of base plate and the carriage plate. In a preferred configuration, the base plate 52 is given a tapered bottom to enable the base plate conveniently sliding through the carriage plate 26.

For locking the base plate 52 to the carriage plate 26 and to prevent the accidental release or twisting of surgical instrument during surgery, an L-shaped bracket 54 (as shown in FIG. 5(a)) is provided at the first end of the base plate 52 that secures the surgical instrument from the top as it slides through the carriage plate 26. Further, when the quick release clip is manually actuated, the retractable locking element gets compressed to allow the quick release clip comfortably sit in the locking slots of the base plate 52. Now, once the base plate 52 is suitably placed over the carriage plate 26, the retractable locking element 44, 46 decompress to lock the surgical instrument 50 therewith the support member 20 thereby preventing any relative motion between the two.

Before the surgical instrument 50 is introduced for the first time in a relatively longitudinal direction with respect to the manipulating end 100(a) of manipulating arm 100, the carriage plate 26, must have, traveled along the linear guide rods 18, 19 towards the proximal end 12(a) of the support member 20 until it reaches its home position. Now, the base plate 52 of the surgical instrument 50 can be made to slide thereon and lock therewith the carriage plate 26, the two plates so held together, hereinafter referred to as the combination plate. The surgical instrument 50 can now be conveniently introduced through the cannula into the body cavity to reach its operational position without getting stuck within the cannula or damaging surrounding tissue.

The combination plate, in one preferred embodiment, travels maximum up to the second safe limit positioned close to distal end 12(b). The distance traveled between the first safe limit and the second safe limit by the combination plate defines its permitted range of motion. In one specific and preferable embodiment, the combination plate can travel up to 600 mm. The combination plate slides along the insertion axis that generally coincides with the remote center of position, which remains fixed relative to the base of the robotic arm 100.

Figure 6:
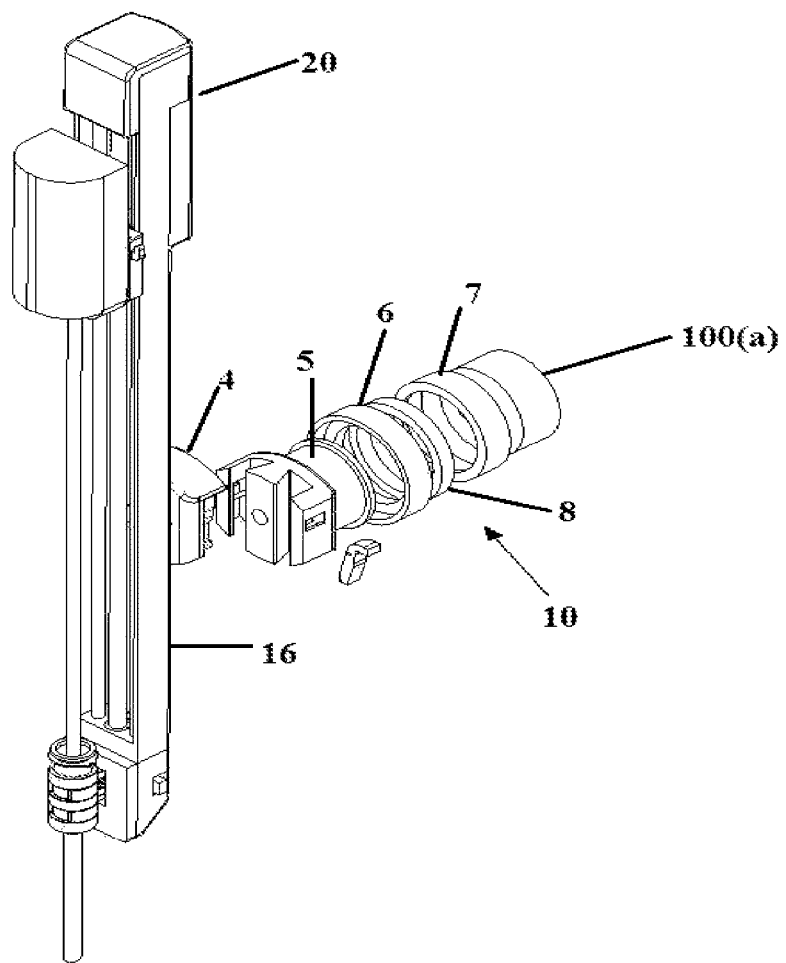
FIG. 6 is an exploded view of the intermediate fastening component in accordance with one embodiment of the present invention.

As shown in FIG. 6, the robotic system 200 further includes a sterile intermediate fastening component 10 to shield non sterile manipulating arm 100 from the sterile field of the surgical site during the procedure. In one embodiment, the intermediate fastening component 10 is manufactured as a reusable component that can be sterilized by normal methods i.e. steam, heat and pressure, chemicals and the like. Referring again to FIG. 6, the intermediate fastening component 10, in one preferred embodiment includes rotating and non rotating mechanical elements, generally, a rotating shaft 5 that is laterally urged through openings provided by a pair of external circular ring members 6 (non rotating) and 7 (rotating), and adapted to turn therein along the axis of the manipulating end 100(a) of the manipulating arm.

While the first end of the shaft 5(a) is slidably connected to a complementary arrangement 4 (as shown in FIG. 6) provided on the second surface 16 of the support member 20, the second end 5(b) is fixedly connected to the manipulating end 100(a) of the manipulating arm 100 as the female connector pins on the shaft 5 at second end 5(b) engage with the corresponding male connector pins provided on the manipulating end 100(a) to establish an electrical connection therewith. The manipulating end 100(a) includes a plurality of electrical connections (not shown) for transferring the motion to the support assembly 20 through drive cables running within shaft 5 (not shown).

The first circular non rotating ring member 6 includes an internal bearing 8 that rests comfortably within the seat defined by the circular ring member 6. In the present configuration, while the internal bearing 8 rotates along the axis of the manipulating end 100(a) and about the rotatable shaft 5, the ring 6 is fixedly held with respect to rotatable internal bearing 8, for the reasons of ease in draping of the robotic system, as will be discussed in later sections. The other rotatable circular ring member 7 includes an internal threaded portion with complementary threaded portion over the manipulating end 100(a) of the manipulating arm 100 so as to threadably couple the two in a sealing relationship. In a preferred configuration, the rotary motion from the manipulating end 100(a) is transferred through the rotating shaft 5, rotating circular ring member 7 and internal bearing 8 to the support assembly.

The shaft 5 towards its end 5(a) facing the second surface 16 of the support assembly 20 includes a ridge and furrow like arrangement complementing a similar arrangement 4 on the second surface 16 of the support assembly 20, involving arrangement of quick release clips, retractable locking element, and an L shaped bracket in a similar fashion as in surgical instrument base plate 52 sliding onto the carriage plate 26. The shaft 5 towards its end facing the support assembly 20 provides a dovetail configuration with a pair of quick release clips laterally protruding therefrom. The first end of each of the quick release clip is pivotally coupled to shaft end 5(a) while the other end is freely movable bearing a side-to-side abutting relationship with a retractable locking element resting alongside the peripheral edges of the shaft end 5(a).

The second surface 16, including an opening accommodates thereupon a complementing ridge and furrow like arrangement 4 that allows the intermediate fastening component 10 to slide therethrough, as in a dovetail configuration, thereby forming a mechanical coupling between the support assembly 20 and the manipulating arm 100. Now, the retractable locking element pushes the release clips inwards towards each other such that the shaft end 5(a) is conveniently received by the support assembly. This mechanism renders the support assembly 20 modular and freely rotatable relative to the manipulating end 100(a).

Due to the complexity in existing systems, it is almost difficult or impractical to attempt to sterilize the entire robotic assembly. Thus a sterile field is established using a sterile drape that is overlaid over the robotic assembly to isolate non sterile environment from the sterile one. In an existing set up a sterile drape to also provide an interface for transferring mechanical and electrical energy. The present disclosure, endeavors to obviate the cumbersome draping mechanism with a simplified process that allows easy draping of the manipulator arm 100, the sterile drape being sized to cover at least a portion of manipulator arm 100, preferably substantially the entire manipulator arm 100, and extending up to the first circular ring member 7 so that most of the components forming part of sterile environment can be sterilized prior to, or following the surgical procedure.

The intermediate fastening component 10 allows free movement of the manipulating end 100(a) and the support assembly 20 without intervening with lengthy drapes stretching up to the cannula holder. In accordance with a preferred embodiment, the sterile drape is unfolded as the drape pockets are sequentially released over the length of manipulating arm 100 and extended up to the first circular ring member 6, which remains stationary with respect to the rotating end of the manipulating arm 100. This eliminate any over constraint on drape or any twisting thereof with rotary movement of the manipulating end 100(a) since the sterile drape is distantly held from the rotating sections of the fastening component 10.

The foregoing description has been directed to one or more specific embodiments of the articulated arm. It will be apparent; however, that other variations and modifications may be made to the described embodiments, with the attainment of some or all of their advantages. Accordingly this description is to be taken only by way of example and not to otherwise limit the scope of the invention, or depart from the basic inventive concepts. All such variations and modifications are to be considered within the scope of the present invention, the nature of which is to be determined from the foregoing description and the appended claims.

What is claimed is:

1. A medical robotic system, comprising: at least one manipulating arm having a manipulating end; at least one medical instrument; and a modular support assembly removably coupled to the manipulating end of the at least one manipulating arm via an intermediate fastening component, and adapted to releasably secure thereupon the at least one medical instrument to cause slidable displacement of the at least one medical instrument independent of the at least one manipulating arm, wherein the modular support assembly comprises an external casing having a proximal and a distal end, the modular support assembly including: a first surface defining a central cavity to house therein a pair of laterally spaced guide rods axially extending between the proximal and distal ends, a threaded shaft positioned relatively between the pair of laterally spaced guide rods, and a carriage plate slidably mounted over the pair of laterally spaced guide rods for carrying the at least one medical instrument; and a second surface including an opening that is sized and dimensioned to receive the intermediate fastening component, and at least one actuating unit that engages with the threaded shaft to cause sliding motion of the at least one medical instrument independent of the at least one manipulating arm.

2. The medical robotic system of claim 1, wherein the modular support assembly is configured to rotate a full 360 degrees with respect to the manipulating end.

3. The medical robotic system of claim 1, wherein electrical signals are transmitted from the manipulating end to the modular support assembly via the intermediate fastening component to control operation and movement of the modular support assembly.

4. The medical robotic system of claim 1, wherein the modular support assembly is independently sterilizable, operatively attachable and detachable to the at least one manipulating arm, thereby obviating a need for extensive drapes, and hence a need for a cumbersome draping mechanism.

5. The medical robotic system of claim 1, wherein the intermediate fastening component is sterilizable and is configured to isolate a non-sterile environment of the at least one manipulating arm from a sterile environment of the modular support assembly and the at least one medical instrument.

6. The medical robotic system of claim 1, wherein the external casing is further provided with a means for holding a cannula towards the distal end, the external casing having a substantially trapezoidal configuration towards its distal end with a flat apex and two opposed downwardly and inwardly sloping legs so as to avoid the modular support assembly from creating an impact on a body wall.

7. The medical robotic system of claim 1, wherein the carriage plate having a first surface upwardly facing towards a proximal end of the modular support assembly, and a second surface facing downwardly towards a distal end of the modular support assembly, provides a predetermined pattern of generally circular slots on the first and second surfaces, the generally circular slots configured for receiving the threaded shaft and the pair of laterally spaced guide rods.

8. The medical robotic system of claim 7, wherein the pair of laterally spaced guide rods engage with linear bearings provided on each of the first and second surfaces of the carriage plate facilitating smooth sliding motion of the carriage plate, balancing axial and radial load, and adjusting frictional force between the pair of laterally spaced guide rods and the carriage plate.

9. The medical robotic system of claim 1, wherein the threaded shaft is threadably coupled with a complementing nut that is further configured to be operatively associated with the carriage plate, wherein the complementing nut traverses the threaded shaft carrying the carriage plate and hence the at least one medical instrument therewith in a direction parallel to an axis of the at least one medical instrument.

10. The medical robotic system of claim 9, wherein the at least one actuating unit disposed on the second surface of the modular support assembly causes rotation of a first helical pear or spur gear meshingly engaged with a second helical gear or a spur gear, which further operatively interacts with the threaded shaft, for transferring rotary motion thereto and eventually translational motion to the complementing nut.

11. The medical robotic system of claim 1, further comprising one or more sensors disposed on the proximal and distal end of the external casing, the one or more sensors disposed on the proximal and distal end of the external casing are in electronic communication with one or more other sensors disposed on an upwardly facing first surface of the carriage plate and a downwardly facing second surface of the carriage plate respectively, to cause the at least one medical instrument to slide over the pair of laterally spaced guide rods within predefined safety limits.

12. The medical robotic system of claim 1, wherein the carriage plate further comprises a pair of release clips protruding laterally from each side of the carriage plate, with a first end of each release clip bearing a pivoting relationship with a respective side of the carriage plate, and a freely movable second end of each release clip bearing a side-to-side abutting relation with a retractable locking element provided along peripheral edges of the carriage plate.

13. The medical robotic system of claim 12, wherein the carriage plate is configured to receive thereupon a base plate of the at least one medical instrument housing a pair of locking slots, so adapted to receive the freely movable second end of each release clip that gets pushed by corresponding retractable locking element inwards when the base plate is forced to slide along the carriage plate.

14. The medical robotic system of claim 13, wherein the base plate of the at least one medical instrument further includes an L-shaped bracket at its first end facing towards a proximal end of the modular support assembly, the L-shaped bracket being configured to secure the base plate of the at least one medical instrument to the carriage plate from its top as it slides therethrough, thereby preventing an accidental release of the base plate of the at least one medical instrument from its top during reciprocating motion of the carriage plate.

15. The medical robotic system of claim 12, wherein the retractable locking element remains normally biased towards its locked position in absence of applied tension, while adapted to displace from the locked position to an unlocked position upon application of applied tension whenever the base plate of the at least one medical instrument is being received by the carriage plate, wherein upon securely positioning the base plate over the carriage plate the retractable locking element resumes its locked position.

16. The medical robotic system of claim 1, wherein the modular support assembly can travel maximum up to 600 mm independent of motion of the at least one manipulating arm.

* * * * *